United States Patent [19]

Carey et al.

[11] Patent Number: 5,422,010

[45] Date of Patent: * Jun. 6, 1995

[54] METHOD FOR INHIBITING SILICA AND SILICATE DEPOSITION

[75] Inventors: William S. Carey, Ridley Park; Andrew Solov, Holland; Libardo A. Perez, Morrisville, all of Pa.

[73] Assignee: Betz Laboratories, Inc., Trevose, Pa.

[*] Notice: The portion of the term of this patent subsequent to Jul. 26, 2011 has been disclaimed.

[21] Appl. No.: 259,954

[22] Filed: Jun. 15, 1994

Related U.S. Application Data

[63] Continuation of Ser. No. 955,569, Oct. 2, 1992, Pat. No. 5,332,505.

[51] Int. Cl.⁶ .............................................. C02F 5/14
[52] U.S. Cl. .................................. 210/697; 210/698; 210/699; 210/701; 252/180; 252/181
[58] Field of Search ............................... 210/696–701; 252/180, 181

[56] References Cited

U.S. PATENT DOCUMENTS

| | | | |
|---|---|---|---|
| 3,578,589 | 5/1971 | Hwa et al. | 210/58 |
| 3,948,792 | 4/1976 | Watsen et al. | 252/181 |
| 4,058,554 | 11/1977 | Guiterrez et al. | 560/180 |
| 4,659,481 | 4/1987 | Chen | 210/697 |
| 4,869,845 | 9/1989 | Chen | 252/181 |
| 4,933,090 | 6/1990 | Gill et al. | 210/701 |
| 5,062,962 | 11/1991 | Brown et al. | 210/698 |
| 5,078,879 | 1/1992 | Gill et al. | 210/701 |
| 5,100,558 | 3/1992 | Brown et al. | 210/701 |
| 5,183,590 | 2/1993 | Carter et al. | 252/392 |
| 5,332,505 | 7/1994 | Carey et al. | 210/697 |

*Primary Examiner*—Peter A. Hruskoci
*Attorney, Agent, or Firm*—Alexander D. Ricci; Richard A. Paikoff

[57] ABSTRACT

A method and composition for inhibiting silica and silicate deposition on metal surfaces in contact with aqueous systems is disclosed.

12 Claims, No Drawings

METHOD FOR INHIBITING SILICA AND SILICATE DEPOSITION

This is a continuation of application Ser. No. 07/955,569 filed Oct. 2, 1992, now U.S. Pat. No. 5,332,505.

FIELD OF THE INVENTION

The present invention relates to cooling and boiler water systems. The control of silica and silicate deposition within these systems is the focus of the invention disclosed hereinafter.

BACKGROUND OF THE INVENTION

The problems of scale formation and its attendant effects have troubled water systems for years. For instance, scale tends to accumulate on internal walls of various water systems, such as boiler and cooling systems, thereby reducing heat transfer properties and fluid flow through heat exchange tubes.

One particular type of deposit, silica, is especially troublesome in some systems. Where the water used in cooling systems and water-cooled industrial heat exchangers is taken directly from lakes, rivers, ponds or municipal water sources, various amounts of dissolved and suspended solids including silica are present. Problems are compounded in open recirculating water systems due to the fact that as water evaporates the silica concentration increases, thereby increasing both the occurrence and degree of deposition.

In cooling water systems, silica and silicate compounds form deposits on the internal metal surfaces in contact with the water flowing through the system. In this manner, heat transfer efficiency becomes severely impeded, which in turn has a deleterious effect on the overall operating efficiency of the cooling water system. Silica and silicate deposition also causes problems on other conduit and pipe surfaces as well as on equipment such as valves, nozzles and pumps.

Although current industrial cooling systems make use of sophisticated external treatments of the feedwater, e.g., coagulation, filtration, softening of water prior to its being fed into the water system, these operations are only moderately effective. In all cases, external treatment does not in itself provide adequate treatment since muds, sludge, silts and dissolved solids such as silica, escape the treatment, and eventually are introduced into the cooling system.

Various methods have been utilized for resolving the problem of sludge and silt, including silica, deposition. In U.S. Pat. No. 3,578,589, Hwa et al., inhibition of scale, mud, silt and sludge deposition is achieved by adding a nonionic surface active agent, such as a polyethyleneoxy alkyl phenol, and a water soluble polymer, such as polyacrylic acid.

In Watsen et al., U.S. Pat. No. 3,948,792, the patentees disclose the problem of silicate scale formation in automobile and diesel coolant systems. They teach adding a water soluble carboxylic acid polymer and nitrites along with either boric acid or borates.

U.S. Pat. No. 4,869,845, Chen, utilizes the same copolymer as utilized in the present invention to treat scale and corrosion problems in cooling and boiler water systems. The copolymer is added to the system with both a phosphonate and a zinc compound. The purpose of the copolymer is to maintain the solubility of zinc. Without this mechanism, the zinc would precipitate in the form of zinc hydroxide and would be unavailable for its desired anti-corrosion activity.

DETAILED DESCRIPTION OF THE INVENTION

In accordance with the invention, it has been discovered that water-soluble compounds comprising the $\alpha$-hydroxy-$\alpha$, $\beta$-dicarboxylic acid functionality as shown in Formula I hereinafter are effective in controlling the formation of silica and silicate deposits on the internal surfaces of structures housing cooling water systems:

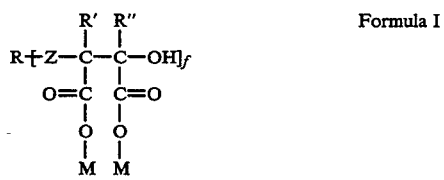

Formula I wherein R is a substituted or non-substituted alkyl or aryl moiety having a carbon chain up to the length where solubility in an aqueous solution is lost, or a repeat unit obtained after polymerization of an ethylenically unsaturated compound; R' and R" are hydrogen, $C_{1-4}$ alkyl or $C_{1-4}$ substituted alkyl; Z is O, S, NH, or NR, where R is as described above; f is a positive integer; and M is hydrogen, a water soluble cation (e.g., $NH_4^+$, alkali metal), or a non-substituted lower alkyl group having from 1 to 3 carbon atoms.

In a preferred embodiment of the invention, R is a substituted or non-substituted $C_6$-$C_{12}$ alkyl or aryl moiety, R' and R" are hydrogen, Z is NH, f is 1-2, and M is $Na^+$.

In a particularly preferred embodiment of the invention, R is a —$CH_2C_6H_4$—$CH_2$—moiety, R' and R" are hydrogen, Z is NH, f is 2, and M is $Na^+$.

The compounds of the present invention can be obtained by the ring opening reaction of a suitable reagent with a salt or ester of epoxysuccinic acid. The general reaction can be represented as follows:

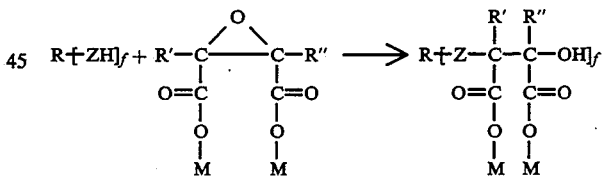

wherein R, R', R", Z, f and M are as described above.

For a general review of ring-opening reactions of epoxides, see March, "Advanced Organic Chemistry-Reactions, Mechanisms, and Structure", 2nd Edition, Chapter 10, McGraw-Hill, New York, 1977.

The reaction can be performed neat, or in aqueous or non-aqueous solvents. If the resulting product is non-aqueous it should be modified by traditional techniques known to those skilled in the art to yield a water soluble product (e.g., hydrolysis of ester derivatives).

In a preferred embodiment of the invention, aqueous solutions of the compounds of the present invention are prepared by reacting a diamine with an aqueous solution of disodium epoxysuccinate ($ESA \cdot Na_2$). The reaction of the ring opening reagent with the disodium epoxysuccinate is typically conducted under atmospheric conditions at about 30° C. to 100° C., preferably from about 80° C. to 100° C. The molar ratio of the ring opening reagent to disodium epoxysuccinate may fall within the range of about 100:1 to 1:100, with a molar ratio of about 1.0:2.1.

The compounds of the present invention should be added to the aqueous system for which silica/silicate inhibition activity of metal parts in contact with an aqueous medium is desired, in an amount effective for the purpose. This amount will vary depending upon the particular system for which treatment is desired and will be influenced by factors such as the area subject to deposition, pH, temperature, water quantity and the respective concentrations in the water of the potential scale and deposit forming species. For the most part, the compounds of the present invention will be effective when used at levels of about 0.1–500 parts per million of water, and preferably from about 5–50 parts per million of water contained in the aqueous system to be treated. The compounds may be added directly into the desired water system in a fixed quantity and in a state of an aqueous solution, continuously or intermittently.

The compounds of the present invention are not limited to use in any specific category of water system. For instance, in addition to cooling and boiler water systems, the compounds may also be effectively utilized in steam generating, gas scrubbing, and pulp and paper process systems and the like wherein the formation and deposition of silica/silicate scale is a problem.

The compounds of the present invention may also be used with topping agent components in order to enhance the scale controlling and corrosion inhibition properties thereof. Such topping components are known to those skilled in the art. For example, details of such compounds are disclosed in U.S. Pat. Nos. 4,659,481 and 5,062,962, both hereby incorporated by reference. It is expected that the compounds of the present invention can be used in conjunction with the polymers and topping components of the above-noted references to provide treatment programs which effectively inhibit corrosion and scale deposition in water systems.

Suitable topping agents include polyacrylates, polyepoxysuccinic acids phosphoric acids and water soluble salts thereof, phosphonic acids and water soluble salts thereof, polyvalent metal salts, chromate compounds, azole compounds and molybdate compounds and mixtures thereof.

A suitable polyacrylate is of the formula:

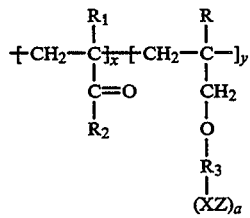

wherein $R_1$ is H or lower alkyl ($C_1$–$C_3$); $R_2$ is OH, OM, or $NH_2$; M is a water soluble cation; $R_3$ is a hydroxy substituted alkyl or alkylene radical having from 1 to 6 carbon atoms or a non-substituted alkyl or alkylene radical having from 1 to 6 carbon atoms; X, when present, is an anionic radical selected from the group consisting of $SO_3$, $PO_3$, $PO_4$ and $CO_2$; Z, when present, is H or any water soluble cations which together counterbalance the valence of the anionic radical; a is 0 or 1; the molar ratio x:y of said polymer being between 30:1 to 1:20.

The polyepoxysuccinic acid is of the formula:

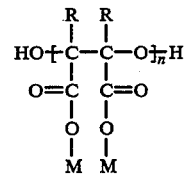

wherein n is from about 1 to 50, M is a water soluble cation and R is H or a $C_1$–$C_4$ alkyl.

The phosphoric acid may be an orthophosphoric acid, primary phosphoric acid, secondary phosphoric acid, pyrophosphoric acid, tripolyphosphoric acid, trimetaphosphoric acid and tetrametaphosphoric acid. The phosphonic acid may be an ethylenediaminetetramethylenephosphonic acid, methylenediphosphonic acid, hydroxyethylidenediphosphonic acid and 2-phosphonobutane-1,2,4-tricarboxylic acid. The azole compound may be 1,2,3-tolyltriazole, benzotriazole, mercaptobenzothiazole and benzothiazole.

The topping agent may be added to the system in an amount of about 1 to 500 parts per million of said system.

EXAMPLES

The invention will now be further described with reference to a number of specific examples which are to be regarded solely as illustrative and not as restricting the scope of the present invention.

Process Example I

Preparation of Aspartic acid, 3-hydroxy, N,N'-[1,4-phenylenebis(methylene)]bis-tetrasodium salt.

A suitable reaction flask was equipped with a reflux condenser, stirrer, thermometer, nitrogen inlet and addition parts. 20.6 grams of p-xylylenediamine (99%, 0.15 mole) and 167 milliliters of deionized water were charged to the flask and purged with nitrogen. 56.4 grams of ESA.Na$_2$ (0.315 mole) was then charged to the flask and the solution mixed at 20° C. for 1 hour, then 90° C. for 12 hours. The batch was cooled to 25° C., diluted with 49 milliliters of deionized water and filtered to yield a clear filtrate.

The structure of the product was verified by $^{13}$C NMR spectroscopy. The yield of product was estimated to be 89 mole % by integration of the methine region of the $^{13}$C NMR spectrum.

Using the above-described preparative techniques, several other bis(α-hydroxy-α, β-dicarboxylic acid) compounds were prepared. The results of these preparations are set forth in Table 1.

TABLE 1

Bis (α-hydroxy -α,β-dicarboxylic acid) Compound Summary

| Example | |
|---|---|
| 1. | Aspartic acid, 3-hydroxy, N,N'-[1,4-phenylenebis(methylene)]bis- tetrasodium salt |
| | R: p-CH$_2$—C$_6$H$_4$—CH$_2$—   Z: —NH—   f: 2 |
| 2. | Aspartic acid, 3-hydroxy, N,N'-[1,3-phenylenebis(methylene)]bis- tetrasodium salt |
| | R: m-CH$_2$—C$_6$H$_4$—CH$_2$—   Z: —NH—   f: 2 |

TABLE 1-continued

Bis (α-hydroxy -α,β-dicarboxylic acid) Compound Summary

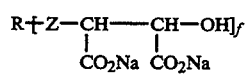

| Example | | | | |
|---|---|---|---|---|
| 3. | Aspartic acid, 3-hydroxy, N,N'-1,10-decanediylbis- tetrasodium salt | | | |
| | R: —CH$_{10}$H$_{20}$— | Z: —NH— | f: 2 | |
| 4. | N,N'-bis(aspartic acid, 3-hydroxy) analog of Texaco Jeffamine ED-600: b = 8.5, a + c = 2.5, approximate MW = 600. | | | |
| | R: —CHCH$_2$-f-OCHCH$_2$]$_a$—[OCH$_2$CH$_2$]$_b$—[OCH$_2$CH]$_c$— | | | |
| | CH$_3$  CH$_3$  CH$_3$ | | | |
| | | Z: —NH— | f: 2 | |
| 5. | Aspartic acid, 3-hydroxy, N,N'-1,2-phenylenebis- tetrasodium salt | | | |
| | R: o-C$_6$H$_4$— | Z: —NH— | f: 2 | |
| 6. | Aspartic acid, 3-hydroxy, N,N'-1,3-phenylenebis- tetrasodium salt | | | |
| | R: p-C$_6$H$_4$— | Z: —NH— | f: 2 | |

Guiterrez et al., U.S. Pat. No. 4,058,554, relates to the preparation of polyfunctional compounds which may be hydrolyzed to the corresponding salts, which in turn are metal sequestering agents. Compounds taught by Guiterrez include the non-hydroxy analogs of the compounds of the present invention. In order to determine if the Guiterrez materials exhibited efficacy as silica-/silicate inhibitors, the non-hydroxy derivatives of Example 1 and Example 4 of the present invention, Comparative Examples 1 and 2 of Table 2 respectively, were prepared for evaluation.

TABLE 2

Bis(α, β-dicarboxylic acid) Compound Summary

TABLE 2

Bis (α,β-dicarboxylic acid) Compound Summary

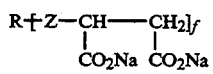

| Com- parative Examples | | | | |
|---|---|---|---|---|
| 1. | Aspartic acid, N,N'-[1,4-phenylenebis(methylene)] bis- tetrasodium salt | | | |
| | R: p-CH$_2$—C$_6$H$_4$—CH$_2$— | Z: —NH— | f: 2 | |
| 2. | Aspartic acid, N,N'-1,6-hexanediylbis- tetrasodium salt | | | |
| | R: —C$_6$H$_{12}$— | Z: —NH— | f: 2 | |

Comparative Examples

1. Aspartic acid, N,N'-[1,4-phenylenebis(methylene)] bis- tetrasodium salt
R: p —CH$_2$—C$_6$H$_4$—CH$_2$—Z: —NH—f: 2
2. Aspartic acid, N,N'-1,6-hexanediylbis-tetrasodium salt
R: —C$_6$H$_{12}$—Z: —NH—f: 2

Applications Example I

Non-Ecaporative Bench Top Recirculator Unit (BTU) Testing

Table 3 summarizes the silica/silicate inhibition results for the compounds of the present invention under dynamic conditions in a non-evaporative laboratory bench top recirculator unit utilizing makeup and blowdown. The system is designed to provide a realistic evaluation of the efficacy of a treatment to prevent deposition on heat transfer surfaces.

The treated water is circulated by a pump over two heat exchanger tubes. A vertically mounted hot heat exchanger tube is fitted with an electrical heater. A horizontally mounted cold heat exchanger tube is maintained at 50° F. by circulating a refrigerant through its interior. The circulating water velocity is independently controlled for each surface. The pH and temperature of the circulating water are automatically controlled, and the blowdown is set by adjusting the rate of addition of the makeup water to the overflow sump.

The experiments were conducted at 300 ppm total silica (as SiO$_2$) and pH 8.5. The compounds of the present invention were evaluated alone and in combination with TTA and polyacrylates on different metallurgy.

Experiments 1 to 11 of Table 3 were conducted with 304 stainless steel metallurgy. Experiment 1 utilized no treatment and exhibited heavy deposition after 2 days. Experiments 2 and 3 showed that the deposition could be completely inhibited utilizing 25 ppm of Examples 1 and 2 respectively. Experiments 4 to 6 showed that Examples 4, 5 and 6 exhibited deposit inhibition but were less effective than Examples 1 and 2 under the test conditions. The non-hydroxy analog of Example 1, Comparative Example 1 was evaluated and found to be significantly less effective than Example 1 in experiment 7. Also, Comparative Example 2 was evaluated and found to be less effective than the compounds of the present invention in Experiment 8. Example 1 was evaluated and found to be effective in combination with copolymer and copolymer/tolyltriazole (TTA) in Experiments 9 and 10. In Experiment 11, a blend of 15 ppm Example 3/35 ppm copolymer exhibited moderate deposition.

Experiments 12 to 14 of Table 3 were conducted with admiralty metallurgy. In Experiment 12, the decrease in efficacy of Example 1 is likely due to the release of copper species from the metal surface into the solution, contributing to an acceleration in the rate of silica polymerization. In Experiments 13 and 14, the use of TTA to control copper corrosion, in conjunction with Example 1, was effective in inhibiting silica deposition on admiralty surfaces.

Experiments 15 and 16, conducted under higher M-alkalinity, were equilibrated with 304 stainless steel metallurgy for one day and then switched to low carbon steel metallurgy for three days. In these tests, 25 ppm of Example 1 and 2 ppm of tolyltriazole were blended with varying amounts of poly[epoxysuccinic acid] (PESA), a CaCO$_3$ inhibitor. At 5 ppm PESA, Experiment 15, a very slight CaCO$_3$ deposition was observed on the hot surface. At 10 ppm PESA, Experiment 16, both surfaces were free of deposit and only light pitting was observed.

TABLE 3

Dynamic Silica Inhibition Tests
Recirculator Units

Conditions:

| | | |
|---|---|---|
| 600 ppm Ca as CaCO$_3$ | | pH = 8.5 |
| 300 ppm Mg as CaCO$_3$ | | Sump T = 120° F. |
| 300 ppm SiO$_2$ | | Flow Rate = 6 gpm (hot surface) |
| 100 ppm NaHCO$_3$ | | 1 gpm (cold surface) |
| 635 ppm Cl | | Heat Flux = 9,090 Btu/ft$^2$/hr |
| 27.4 ppm Na | | Metallurgy as noted |
| | | Duration as noted (days) |

TABLE 3-continued

Dynamic Silica Inhibition Tests
Recirculator Units

| Experiment No. and Treatment | ppm (actives) | Hot Surface Appearance-Metallurgy-Duration | Cold Surface Appearance-Metallurgy-Duration |
|---|---|---|---|
| 1. No treatment | | 5-SS-2 | 5-SS-2 |
| 2. Example 1 | 25 | 1-SS-2 | 1-SS-2 |
| 3. Example 2 | 25 | 1-SS-2 | 1-SS-2 |
| 4. Example 4 | 25 | 2-SS-2 | 2-SS-2 |
| 5. Example 5 | 25 | 2-SS-2 | 2-SS-2 |
| 6. Example 6 | 25 | 3-SS-2 | 3-SS-2 |
| 7. Comparative Example 1 | 25 | 3-SS-2 | 3-SS-2 |
| 8. Comparative Example 2 | 25 | 4-SS-2 | 4-SS-2 |
| 9. Example 1 Acrylic copolymer* | 22 35 | 1-SS-2 | 1-SS-2 |
| 10. Example 1 Acrylic copolymer TTA | 25 35 2 | 1-SS-2 | 2-SS-2 |
| 11. Example 3 Acrylic copolymer | 15 35 | 4-SS-2 | 4-SS-2 |
| 12. Example 1 | 25 | 3-Adm-2 | 2-SS-2 |
| 13. Example 1 TTA | 25 2 | 1-Adm-3 | 1-Adm-3 |
| 14. Example 1 TTA | 25 3 | 1-Adm-2 | 1-Adm-2 |
| 15. Example 1 TTA PESA*** | 25 2 5 | 1-SS-1 2-LCS-3 | 1-SS-1** 1-LCS-3 |
| 16. Example 1 TTA PESA | 25 2 10 | 1-SS-1 1-LCS-3 | 1-SS-1** 1-LCS-3 |

Deposition Rating:
1 = clean, no visible deposition
2 = very slight deposit, almost none visible
3 = slight deposit, thin film of deposit
4 = moderate deposit, thick film of deposit
5 = heavy deposit, surface not visible because totally covered by thick deposit Metallurgy:
SS = 304 Stainless Steel
Adm = Admiralty
LCS = Low Carbon Steel

*See Chen, U.S. Pat. No. 4,659,481
**350 ppm NaHCO₃/switched metallurgy
***See Brown, U.S. Pat. No. 5,062,962

Applications Example II

Mini-Evaporative Laboratory Tower (Mini-ELT) Testing

Table 4 summarizes the silica/silicate inhibition results for Example 1 of the present invention under dynamic conditions in a mini-evaporative laboratory tower (mini-ELT) unit. The mini-ELT unit is designed to simulate the evaporation, windage, makeup and blowdown processes of an open recirculating cooling system.

The makeup water of a mini-ELT is pump fed to the sump of the tower. A float valve controls the influx of the makeup water to maintain a constant sump level. Water loss from the system is due to blowdown, evaporation and windage. Windage (uncontrollable blowdown) occurs in the mini-ELT when circulating water entering the top of the tower above the highest splash deck is pulled into the ventilation system by a fan at the top of the unit.

These water losses are taken into account when the treatment is fed by monitoring the recirculating water conductivity. The recirculating water conductivity is regulated by a conductivity controller and a blowdown pump. At the beginning of the experiment, the makeup conductivity is measured, and the blow down control point is set to the calculated conductivity corresponding to the desired cycles of concentration. When the recirculating water conductivity exceeds the blowdown set point, the blowdown pump is activated.

The treated water is circulated by a pump over two heat exchanger tubes. A vertically mounted hot heat exchanger tube is fitted with an electrical heater. A horizontally mounted cold heat exchanger tube is maintained at room temperature. The circulating water velocity is independently controlled for each surface. The pH and temperature of the circulating water are automatically controlled. Carbon dioxide was utilized to control the pH in the experiments.

Thirty ppm of Example 1 was able to maintain both 304 stainless steel tubes clear of deposition after 14 days at 5 cycles in Experiment 1. A slight deposition on both tubes was observed after increasing the cycles to 6.5 and holding for 6 days.

In Experiment 2, the hot tube of metallurgy was changed to admiralty, and 4 ppm of tolyltriazole (TTA) was added to the treatment. Both tubes were free of deposition after 14 days at 5 cycles. A slight deposition on the cold 304 stainless steel tube was observed after increasing the cycles to 6.5 and holding for 6 days, while the hot admiralty tube remained clean.

Experiment 3 was similar to Experiment 2, except that 35 ppm of Example 1 was blended with 4 ppm of TTA and 5 ppm of poly[epoxysuccinic acid] (PESA), and the pH was 8.8. Both tubes were free of scale after 12 days at 5 cycles.

TABLE 4

Dynamic Silica Inhibition Tests
Mini-Evaporative Laboratory Tower (mini-ELT) Units

| Makeup Water: | |
|---|---|
| 120 ppm Ca as CaCO₃ | pH as noted |
| 60 ppm Mg as CaCO₃ | Sump T = 120° F. |
| 60 ppm SiO₂ | Flow Rate = 4 gpm (hot surface) |
| 30 ppm M-alk as CaCO₃ | 4 gpm (cold surface) |
| Conductivity: | |
| 550 umhos | Heat Flux = 15,600 Btu/ft²/hr |
| | Metallurgy as noted |
| | Cycles as noted |
| | Duration as noted (days) |

| Experiment No. and Treatment | ppm (Actives) | pH | Cycles | Hot Surface Appearance-Metallurgy-Duration | Cold Surface Appearance-Metallurgy-Duration |
|---|---|---|---|---|---|
| 1. Example 1 | 30 | 8.5 | 5.0 6.5 | 1-SS-14 3-SS-6 | 1-SS-14 3-SS-6 |
| 2. Example 1 TTA | 30 4 | 8.5 | 5.0 6.5 | 1-Adm-14 1-Adm-6 | 1-SS-14 2-SS-6 |
| 3. Example 1 TTA PESA | 35 4 5 | 8.8 | 5.0 | 1-Adm-12 | 1-SS-12 |

Deposition Rating:
1 = clean, no visible deposition
2 = very slight deposit, almost none visible
3 = slight deposit, thin film of deposit
4 = moderate deposit, thick film of deposit
5 = heavy deposit, surface is not visible because it is totally covered by a very thick deposit
Metallurgy:
SS = 304 Stainless Steel
Adm = Admiralty

Applications Example III

Controlled Evaporation Research Tower (CERT) Testing

Table 5 summarizes the results of the evaporative experiments conducted using a controlled evaporation research tower (CERT) unit. The CERT unit is similar in design to the mini-ELT. In these experiments, the number of cycles was determined by the ratio of the makeup and blowdown rates, and no cold exchanger tube was utilized. Under these test conditions, 25 ppm of Example 1 in combination with 6 ppm of 1-hydroxyethylidenediphosphonic acid (HEDP), 3 ppm of tolyltriazole (TTA) and 30 ppm of acrylic copolymer, did not result in an increase in deposit inhibition. This level of material may have been unsuitable under these harsher reaction conditions.

TABLE 5

Dynamic Silica Inhibition Tests
Controlled Evaporation Research Tower (CERT) Units Conditions:
| | |
|---|---|
| 1820 ppm Ca as CaCO3 | pH = 8.2 |
| 840 ppm Mg as CaCO3 | Sump T = 120° F. |
| 250 ppm SiO2 | Flow Rate = 4 gpm (hot surface) |
| 520 ppm M-alk as CaCO3 | Heat Flux = 8,000 Btu/ft²/hr |
| 1290 ppm Cl | Metallurgy as noted |
| 3670 ppm SO4 | Duration as noted (days) |

| Experiment No. and Treatment | ppm (actives) | Hot Surface Appearance- Metallurgy- Duration | Corrosion Rate |
|---|---|---|---|
| 1. Acrylic copolymer | 30 | 3-LCS-6 | 3.2–5.0 mpy |
|    TTA | 3 | | |
|    HEDP | 6 | | |
| 2. Example 1 | 25 | 3-LCS-7 | 3.2–5.0 mpy |
|    Acrylic copolymer | 30 | | |
|    TTA | 3 | | |
|    HEDP | 6 | | |

Deposition Rating:
1 = clean, no visible deposition
2 = very slight deposit, almost none visible
3 = slight deposit, thin film of deposit
4 = moderate deposit, thick film of deposit
5 = heavy deposit, surface is not visible because it is totally covered by a very thick deposit
Metallurgy:
LCS = Low Carbon Steel While we have shown and described herein certain embodiments of the present invention, it is intended that there be covered as well any change or modification therein which may be made without departing from the spirit and scope of the invention.

We claim:

1. A method of inhibiting the deposition of silica and silicate compounds on the metal surfaces in contact with an aqueous system comprising adding to the system a sufficient amount for the purpose of a compound having the formula:

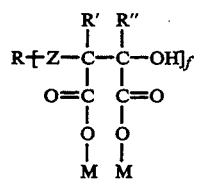

wherein R is a —$CH_2C_6H_4CH_2$— moiety; R' and R" are hydrogen, $C_{1-4}$ alkyl or $C_{1-4}$ substituted alkyl; Z is NH, NR, O or S; f is a positive integer; and M is H, a water soluble cation or a $C_1$–$C_3$ alkyl group.

2. The method as recited in claim 1 further comprising adding to said aqueous system a sufficient amount for the purpose of a topping agent selected from the group consisting of polyacrylates, polyepoxysuccinic acids phosphoric acids and water soluble salts thereof, phosphonic acids and water soluble salts thereof, polyvalent metal salts, chromate compounds, azole compounds and molybdate compounds and mixtures thereof.

3. The method as recited in claim 2 wherein said polyacrylate has the formula:

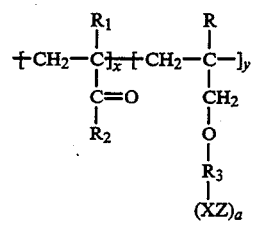

wherein each $R_1$ is independently H or lower alkyl ($C_1$–$C_3$); $R_2$ is OH, $NH_2$ or M; M is a water soluble cation; $R_3$ is a hydroxy substituted alkyl or alkylene radical having from about 1 to 6 carbon atoms; X is $SO_3$, $PC_3$, $PC_4$ or $CO_2$; Z is H or a water soluble cation or cations; a is 0 or 1; and the molar ratio of x:y is from about 30:1 to 1:20.

4. The method as recited in claim 2 wherein said polyepoxysuccinic acid has the formula:

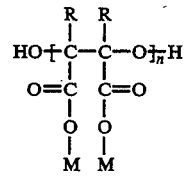

wherein n is from about 1 to 50, M is a water soluble cation and R is H or a $C_1$–$C_4$ alkyl.

5. The method as recited in claim 2 wherein said phosphoric acid is selected from the group consisting of orthophosphoric acid, primary phosphoric acid, secondary phosphoric acid, pyrophosphoric acid, tripolyphosphoric acid, trimetaphosphoric acid and tetrametaphosphoric acid.

6. The method as recited in claim 2 wherein said phosphonic acid is selected from the group consisting of ethylenediaminetetramethylenephosphonic acid, methylenediphosphonic acid, hydroxyethylidenediphosphonic acid and 2-phosphonobutane-1,2,4-tricarboxylic acid.

7. The method as recited in claim 2 wherein said azole compound is selected from the group consisting of 1,2,3-tolyltriazole, benzotriazole, thiazole, mercaptothiazole, butylbenzotriazole, mercaptobenzothiazole and benzothiazole.

8. The method as recited in claim 2 wherein said topping agent is added to said system in an amount of about 1 to 500 parts per million of said system.

9. The method as recited in claim 1 wherein said aqueous system is a cooling water system.

10. The method as recited in claim 1 wherein said aqueous system is a steam generating system.

11. The method as recited in claim 1 wherein said aqueous system is a gas scrubbing system.

12. The method as recited in claim 1 wherein said aqueous system is a pulp and paper process system.

* * * * *